United States Patent [19]
Minekane

[11] Patent Number: 4,906,433
[45] Date of Patent: Mar. 6, 1990

[54] AUTOMATIC CHEMICAL ANALYZER

[75] Inventor: Tomiharu Minekane, Ootawara, Japan

[73] Assignee: Kabushiki Kaisha Toshiba, Kawasaki, Japan

[21] Appl. No.: 318,445

[22] Filed: Feb. 28, 1989

Related U.S. Application Data

[63] Continuation of Ser. No. 64,552, Jun. 22, 1987, abandoned.

[30] Foreign Application Priority Data

Jun. 24, 1986 [JP]  Japan ................................. 61-146064

[51] Int. Cl.⁴ ............................................ G01N 35/04
[52] U.S. Cl. ........................................ 422/64; 422/67; 422/100
[58] Field of Search ............................. 422/64, 67, 100

[56] References Cited

U.S. PATENT DOCUMENTS

| | | | |
|---|---|---|---|
| 4,325,910 | 4/1982 | Jordan | 422/64 |
| 4,459,265 | 7/1984 | Berglund | 422/64 |
| 4,549,809 | 10/1985 | Minekane | 422/64 |
| 4,629,703 | 12/1986 | Uffenheimer | 422/64 |
| 4,647,432 | 3/1987 | Wakatake | 422/64 |
| 4,699,766 | 10/1987 | Yamashita | 422/64 |
| 4,774,055 | 9/1988 | Wakatake | 422/64 |

Primary Examiner—Micheal S. Marcus
Assistant Examiner—D. John Griffith, Jr.
Attorney, Agent, or Firm—Oblon, Spivak, McClelland, Maier & Neustadt

[57] ABSTRACT

An automatic chemical analyzer having a plurality of reaction tubes which are mounted on a first turntable and held in a first circle. A first motor drives the first turntable such that the reaction tubes move along the first circle. A sampling nozzle distributes a sample to the reaction tubes. A plurality of first reagent vessels containing different reagents of a first group are mounted on a second turntable and held in a second circle concentric with the first circular path. A second motor drives the second turntable such that the first reagent vessels move along the second circle. A plurality of second reagent vessels containing different reagents of a second group are fixedly held in a third circle intersecting with the first and second circular paths. A reagent-distributing nozzle is moved along the third circle, thereby to distribute a reagent to the reaction tubes from any one of the first reagent vessels or any one of the second reagent vessels, or both.

5 Claims, 4 Drawing Sheets

AUTOMATIC CHEMICAL ANALYZER

This is a continuation of Ser. No. 064,552, filed 6/22/87, now abandoned.

BACKGROUND OF THE INVENTION

The present invention relates to an automatic chemical analyzer which automatically performs a chemical analysis of samples.

Most of the conventional automatic chemical analyzers are of a multi-channel, multi-item type. The recent tendency has been toward a single-channel, multi-item analytic type, due to the demand that medical expenses be reduced, and, correspondingly, the cost of medical analysis be lowered. Therefore, demand is made for the development of an analyzer which can decrease the waste of reagents required for chemical analysis as much as possible.

A random-access method is known which can minimize the waste of reagents. This method is to distribute the reagent, which is necessary for analyzing a sample, to reaction tubes containing the sample. Generally, a nozzle is used to draw a required amount of the reagent and pipette this amount into the reaction tubes. This method can save reagents, unlike the conventional method wherein a reagent is poured from a container into the reaction tubes through a tube.

The random-access method can be classified into two categories. The method of the first category comprises the steps of moving reagent vessels in a circle, bringing the vessel containing any desired reagent to a predetermined position, withdrawing the reagent from the vessel by a nozzle at said position, transporting the nozzle to the required reagent-pipetting position, and pouring the reagent from the nozzle into the reaction tube located in said pipetting position. In the method of the second category, vessels containing different reagents are fixed at positions. This method comprises the steps of transporting a nozzle to one vessel containing the desired reagent, drawing the reagent from the vessel by the nozzle, bringing the nozzle to a reaction tube, and pouring the reagent from the nozzle into the reaction tube. The random-access method of the first category is predominantly used due to its high operability and efficiency.

The random-access method of the first category will now be described in detail, with reference to FIG. 1 which shows a conventional automatic analyzer. A number of reaction tubes 2 are set in first circle 4. They are intermittently transported along circle 4, for a predetermined pitch (one rotation+one pitch) at each time. A sample has been pipetted into the reaction tubes by a sampling nozzle (not shown). A plurality of reagent containers 6 are set in second circle 8 located adjacent to first circle 4, and are transported in second circle 8. Reagent-pipetting nozzle 10 is held by arm 12. As arm 12 rotates, nozzle 10 moves in arc 14 bridging both circular paths 4 and 8. When tube 2 containing a desired sample reaches reagent-pipetting position 16, reagent vessel 6 containing the reagent, which should be reacted with the sample to analyze the sample, is located in reagent-drawing position 18. A prescribed amount of the reagent is drawn from vessel 6 by nozzle 10 at position 18. Then, arm 12 is rotated, thus bringing nozzle 10 to position 16, where the reagent is poured from nozzle 10 into reaction tube 2. The reagent thereby starts reacting with the sample within reaction tube 2. Upon lapse of a predetermined period, the reaction condition within tube 2 is detected by colorimeter 20. More specifically, lens 24 focuses the light emitted from lamp 22 on reaction tube 2. The light passing through tube 2 passes through slit 26 and is reflected by concave grating 28, and reaches light-receiving element 30.

Recently, a clinical examination, involving a large variety of analyses, i.e., biochemical analysis, serum analysis, and medicine analysis, and the like, is performed by one and the same chemical analyzer. Therefore, an automatic random-access chemical analyzer is demanded which can quickly carry out such a clinical examination.

In order to accomplish a high-speed examination, numerous analyses must be carried out within a short time. When various analyses are performed at high speed, reagents are consumed in great quantities. Hence, in the conventional automatic chemical analyzer, it is necessary to use many reagent vessels for storing at least a one-day requirement of each reagent. The reagent storage will inevitably become expansive. Thus, it takes a long time to transport the vessel containing the desired reagent to the reagent-drawing position. Consequently, the pipetting of a reagent is slowed down, and a high-speed clinical examination cannot be accomplished. Further, the more analysis items, the more reagent vessels, including those containing seldom required ones, must be arranged. Hence, the reagent storage must be even larger.

SUMMARY OF THE INVENTION

It is accordingly the object of the present invention to provide an automatic chemical analyzer which can perform a high-speed analysis, regardless of the number of the items to be analyzed and the quantities of reagent required for the analysis.

According to the present invention, there is provided an automatic chemical analyzer comprising:
- a plurality of reaction tubes; first holding means for holding said reaction tubes a first circle;
- first drive means for driving said first holding means such that said reaction tubes move in the first circle;
- sample-distributing means for distributing a sample to said reaction tubes;
- a plurality of first reagent vessels containing different reagents of a first group;
- second holding means for holding said first reagent vessels in a second circle concentric with said first circle;
- second drive means for driving said second holding means such that said first reagent vessels move in the second circle;
- a plurality of second reagent vessels containing different reagents of a second group;
- third holding means for holding said second reagent vessels in a third circle intersecting with said first and second circles; and
- reagent-distributing means having a nozzle movable in the third circle, for distributing a reagent to said reaction tubes from a reagent vessel held in at least one of said second and third circles.

In the automatic analyzer of this invention, the reaction tubes are held and moved in the first circle, the first reagent vessels are held and moved in the second circle concentric with the first circle, and the second reagent vessels are held in the third circle. When more reagent vessels need to be used, they are held in the third circle, making it unnecessary to increase the number of reagent vessels held and moved in the second circle. Hence, the time required to move any first reagent vessel to the position where the reagent is drawn by the nozzle can be short. Further, the second reagent vessels need not be moved, since they are arranged in the third circle in which the nozzle can move.

DETAILED DESCRIPTION OF THE PREFERRED EMBODIMENTS

Figure 1:
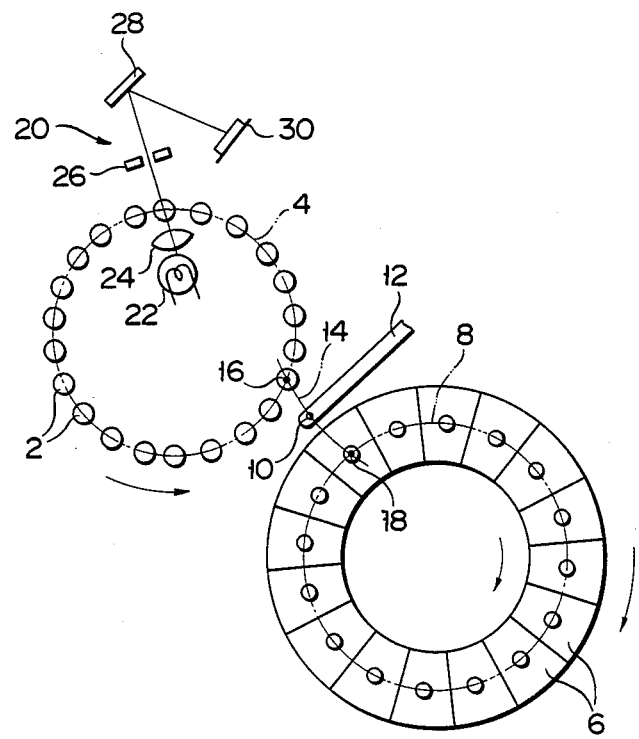
FIG. 1 is a diagram schematically showing part of a conventional automatic chemical analyzer.
Figure 2:
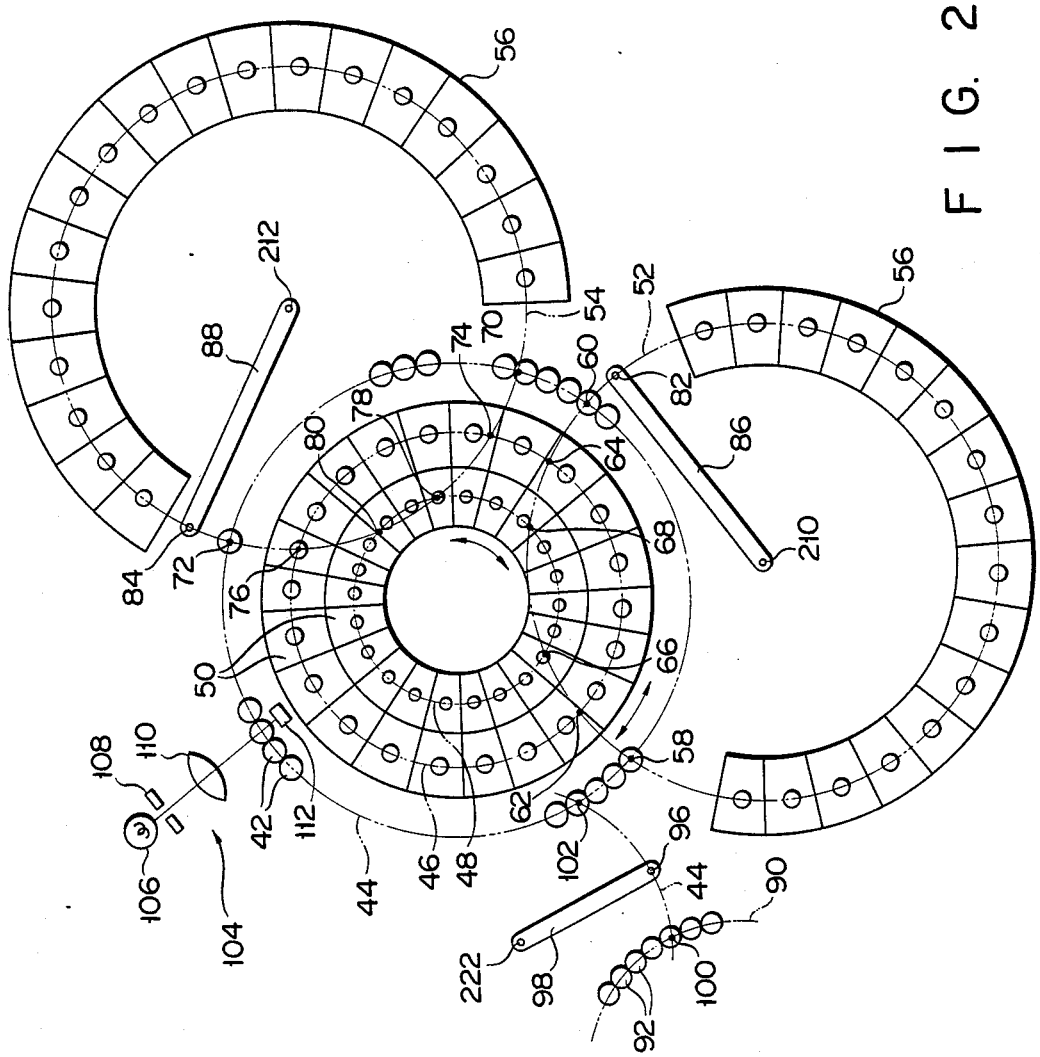
FIG. 2 is a diagram schematically illustrating part of an automatic chemical analyzer according to a first embodiment of the invention.

In FIG. 2, three concentric circles 44, 46 and 48 are drawn. First circle 44 surrounds second circle 46, which in turn surrounds third circle 48. A number of reaction tubes 42 are held in first circle 44. Reagent vessels 50 are held in second and third circles 46 and 48. Reagent vessels 50 contain reagents which are frequently used.

Fourth and fifth circles 52 and 54 are drawn in FIG. 2. Both circles 52 and 54 intersect with first, second and third circles 44, 46 and 48. Reagent vessels 56 are held in arcs of the fourth and fifth circles 52 and 54, each arc having an angle of 180° or more. Some of these vessels 56 contain reagents which are seldom used, and the others contain the same reagents as contained in reagent vessels 50 in second and third circles 46 and 48. Fourth circle 52 intersects with first circle 44 at two points 58 and 60, with second circle 46 at two points 62 and 64, and with third circle 48 at two points 66 and 68. Points 58 and 60 will hereinafter called "first reagent-distributing position" and "second reagent-distributing position," respectively. Points 62 and 64 will be called "first reagent-drawing position" and "second reagent-drawing position." Points 66 and 68 will be referred to as "third reagent-drawing position" and "fourth reagent-drawing position." Fifth circle 54 intersects with first circle 44 at two points 70 and 72, with second circle 46 at two points 74 and 76, and with third circle 48 at two points 78 and 80. Points 70 and 72 will be hereinafter called "third reagent-distributing position" and "fourth reagent-distributing position." Points 74 and 76 will be referred to as "fifth reagent-drawing position" and "sixth reagent-drawing position." Points 78 and 80 will be called "seventh reagent-drawing position" and "eighth reagent-drawing position," respectively.

First reagent-distributing nozzle 82 is supported by rotatable arm 86, and second reagent-distributing nozzle 84 is supported by rotatable arm 88. Arm 86 can rotate to move nozzle 82 in fourth circle 52. Arm 88 can rotate to move nozzle 84 in fifth circle 54.

As is shown in FIG. 2, sixth circle 90 is provided adjacent to first circle 44. A number of sample vessels 92 are held in sixth circle 90. These vessels 92 contain different samples which will be analyzed.

Rotatable arm 98 is provided between first and fourth circular path 44 and 90. Sampling nozzle 96 is supported by arm 98. Arm 98 can rotate such that sampling nozzle 96 moves in arc 94 which intersects with first circle 44 at point 102, and with sixth circle 90 at point 100. Points 100 and 102 will hereinafter called "sample-drawing position" and "sample-distributing position," respectively.

Colorimeter 104 is provided beside first circle 44, in order to detect the color changes of the sample-reagent mixture within any reaction tube 42, thereby to determine the degree of the reaction occurring in tube 42. Colorimeter 104 has light source 106, slit 108, lens 110, mirror 112, and some other parts.

Figure 3:
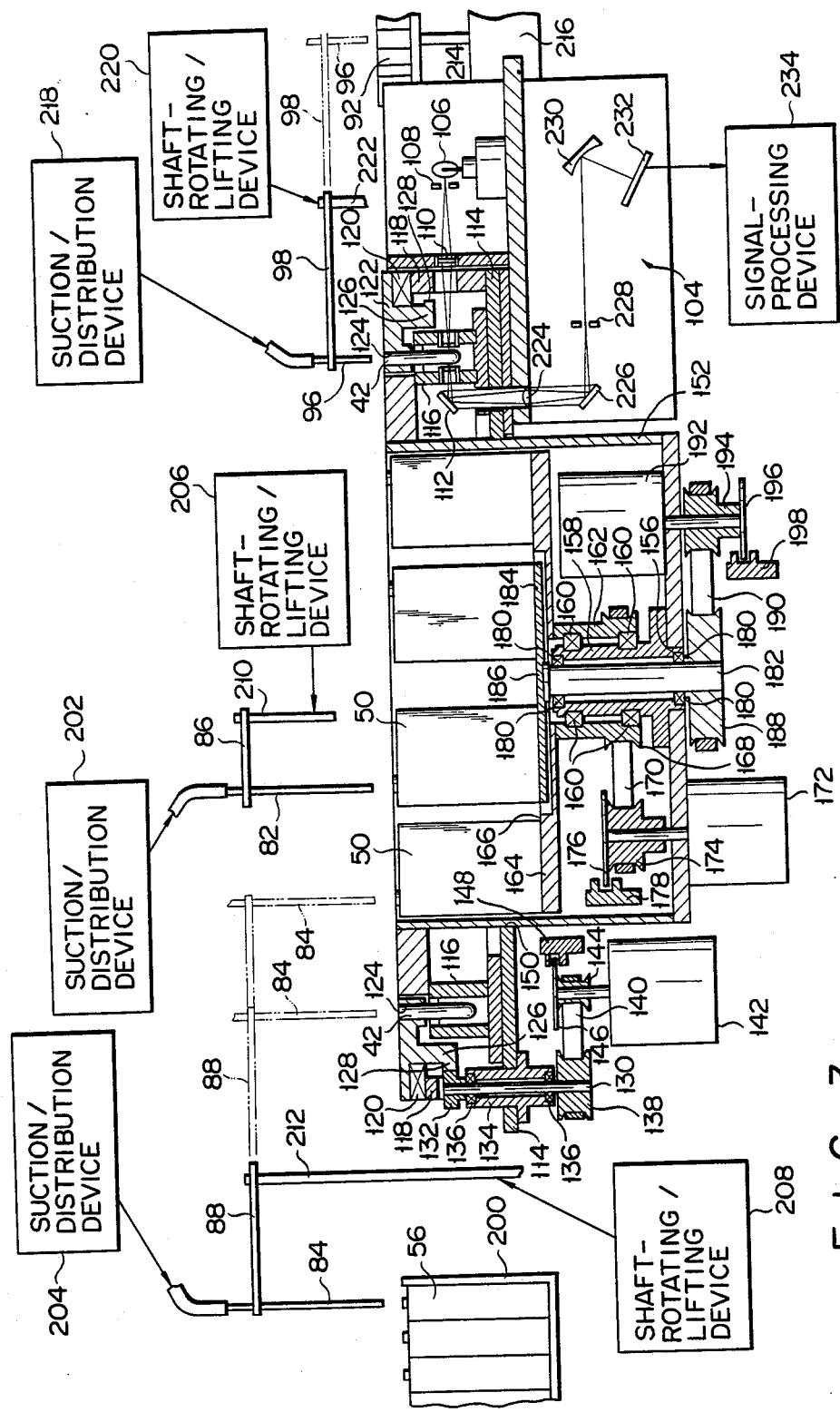
FIG. 3 is a cross-sectional view of the analyzer shown in FIG. 2.

As is illustrated in FIG. 3, base 114 is provided. Annular thermostat bath 116 is mounted on base 114. Annular guide 118 surrounds annular thermostat bath 116. Guide 118 is concentric with annular thermostat bath 116, and a predetermined gap is provided between bath 116 and guide 118. Annular bearing 120 is mounted on the upper edge of annular guide 118, and supports the peripheral edge of ring-shaped first turntable 122. Turntable 122 has holes 124 cut in the inner peripheral edge. Reaction tubes 42 are inserted in these holes 124, and are thereby held in first circle 44. As first turntable 122 rotates, reaction tubes 42 moves in first circle 42, with their lower portions kept immersed within thermostat path 116.

Cylindrical member 126 projects downward from the lower surface of first turntable 122. Teeth 128 are formed on the outer periphery of the lower portion of cylindrical member 126. These teeth 128 are in mesh with gear 132 mounted on the upper end of shaft 130. Shaft 130 is rotatably supported by bearing 136 fitted in cylindrical support 134 fastened to, and penetrating, base 114. Shaft 130 is longer than cylindrical support 134, and thus protrudes from the upper and lower ends of support 134. Pulley 138 is fastened to the lower end of shaft 130. Pulley 144 is fixed to the shaft of motor 142. Belt 140 is wrapped around pulleys 138 and 142. Therefore, first turntable 122 can be rotated by motor 142. More specifically, motor 142 is intermittently rotated, each time through a predetermined angle. First turntable 122 thereby rotates intermittently, each time through a prescribed angle, whereby reaction tubes 42 are moved intermittently, for a predetermined pitch (one rotation + one pitch) at each time. Timing disk 146 is attached to pulley 144. The rotational position of timing disk 146 is detected by detector 148. The rotational position of first turntable 122 is thereby detected, too.

Base 114 has center hole 150 concentric with first turntable 122. Cylinder 152 is fitted in center hole 150. Support disk 154 is fastened to the lower end of cylinder 162. Support disk 154 has center hole 156 concentric with first turntable 122. The lower end of inner cylinder 158 is fitted in this center hole 156.

Outer cylinder 162 is provided, surrounding inner cylinder 158 and being coaxial therewith. Bearings 160 are interposed between inner and outer cylinders 158 and 162. The upper end of outer cylinder 162 is connected to ring-shaped second turntable 164 which is concentric with first turntable 122. Vessel holder 166 is provided on second turntable 164, for holding reagent vessels 50 in second circular path 46. Pulley 168 is integrally formed with outer cylinder 162. Pulley 174 is fastened to the shaft of motor 172. Belt 170 is wrapped around pulleys 168 and 174. Therefore, motor 172 can rotates second turntable 164, thereby to move reagent vessels 50 held in second circular path 46. Timing disk 176 is attached to pulley 174. The rotational position of timing disk 176 is detected by detector 178. Hence, the rotational position of second turntable 164 can be detected, too.

Shaft 182 is rotatably supported by bearing 180 interposed between shaft 182 and the center hole cut in support disk 154. Shaft 182 extends through inner cylinder 158, and its upper end is connected to ring-shaped third turntable 184 which is concentric with first turntable 122. Vessel holder 186 is provided on third turntable 184, for holding reagent vessels 50 in third circular path 48. The lower end portion of shaft 182 downwardly from support disk 154. Pulley 188 is fastened to the lower end of shaft 182. Pulley 194 is fastened to the shaft of motor 192. Belt 190 is wound around these pulleys 188 and 194. Hence, motor 192 can rotate third turntable 184. As third turntable 184 is rotated by motor 192, reagent vessels 50 held by vessel holder 186 are moved in third circle 48. Timing disk 196 is attached to pulley 194. The rotational position of timing disk 196 is detected by detector 198, whereby the rotational position of third turntable 184 is also detected.

As is shown in FIG. 3, stationary reagent storage 200 is provided. In reagent storage 200, reagent vessels 56 are arranged in first and second arcuate paths 52 and 54.

First reagent-distributing nozzle 82 is connected to suction/distribution 202, and second reagent-distributing nozzle 84 is connected to suction/distributing 204. Arm 86 supporting nozzle 82 is supported by shaft 210 which is rotated and vertically moved by shaft-rotating-/lifting device 206. Arm 88 supporting nozzle 84 is supported by shaft 212 which is rotated and vertically moved by shaft-rotating/lifting device 208.

Sample vessels 92 are mounted on fourth turntable 214. Fourth turntable 214 is rotated by motor 216. Sampling nozzle 96 is connected to suction/distributing 218. Arm 98 supporting sampling nozzle 96 is supported by shaft 222 which is rotated and vertically moved by shaft-rotating/lifting device 220.

Light source 106 emits light. The light is applied through slit 108 to lens 110. Lens 110 focuses the light on the sample-reagent mixture contained in reaction tube 42. The light, which has passed through reaction tube 42 is reflected from mirror 112 to light-receiving element 232 via focusing lens 224, mirror 226, slit 228, and concave grating 230. Light receiving element 232 converts the light into an electric signal. The signal is processed by signal-processing device 234.

The operation of the automatic analyzer shown in FIGS. 2 and 3 will now be explained.

When any empty reaction tube 42 reaches sample-distributing position 102, sampling nozzle 96 draws the desired sample from sample vessels 92 located in sample-drawing position 100. Arm 98 is then rotated, thus bringing sampling nozzle 96 to sample-distributing position 102. In this position, sampling nozzle 96 distributes the sample to reaction tube 42.

When reaction tube 42, now containing the sample, reaches first reagent-distributing position 58, first reagent-distributing nozzle 82 draws any desired reagent from reagent vessel 50 located in first reagent-drawing position 62 and held in second circle 46, from reagent vessel 50 located in third reagent-drawing position 66 and held in third circle 48, or from reagent vessel 56 held in first arcuate path 52. Then, nozzle 82 is moved to first reagent-distributing position 58. In position 58, nozzle 82 distributes the reagent to reaction tube 42. At this time, the vessels containing the reagent, which is used in great quantities every day and contained in none of vessels 50 held in second circle 46 or third circle 48, are provided in reagent storage 200 and held in fourth circle 52 and fifth circle 54. When the desired reagent is contained in vessel 56 held in fourth circle 52, first reagent-distributing nozzle 82 is moved to this vessel 56, and draws the reagent from vessel 56. Then, nozzle 82 is moved to first reagent-distributing position 58. In this position 58, the reagent is distributed to reaction tube 42.

When reaction tube 42 further moves and reaches second reagent-distributing position 60, first reagent-distributing nozzle 82 can distribute any desired reagent to reaction tube 42 from reagent vessel 50 held in either second circle 46 or third circle 48, or from reagent vessel 56 held in fourth circle 52 or reagent storage 200.

First reagent-distributing nozzle 82 can distribute the same reagent twice, in first reagent-distributing position 58 for the first time, and in second reagent-distributing position 60 for the second time. A reagent which requires a long time to react thoroughly with the sample is distributed to reaction tube 42 in first reagent-distributing position 58, and a reagent which quickly reacts with the sample is distributed to tube 42 in second reagent-distributing position 60.

When reaction tube 42 moves to third reagent-distributing position 70, second reagent-distributing nozzle 84 draws any desired reagent from reagent vessel 50 located in fifth reagent-drawing position 74 and held in second circle 46, or from reagent vessel 50 located in sixth reagent-drawing position 78 and held in the third circle 48, on from reagent vessel 56 held in fifth circle 56. Then, nozzle 84 is moved to second reagent-distributing position 70. In this position 70, nozzle 84 distributes the reagent to reaction tube 42. When the desired reagent is contained in none of vessels 50 held in second and third circles 46 and 48, but is contained in any reagent-vessel 56 held in fifth circle 54, second reagent-distributing nozzle 84 is moved to the vessel 56 containing the desired reagent, and draws the reagent therefrom. Nozzle 84 is then moved to third reagent-distributing position 70, and distributes the reagent to reaction tube 42.

Reaction tube 42 is further moved forward. When it reaches fourth reagent-distributing position 72, second reagent-distributing nozzle 84 can distribute any desired reagent to reaction tube 42 from reagent vessel 50 held in either second circle 46 or third circle 48, or from reagent vessel 56 held in fifth circle 54 of reagent storage 200.

Second reagent-distributing nozzle 84 can distribute the same reagent twice, in third reagent-distributing position 72 for the second time. Moreover, a reagent which requires a long time to react completely with the sample is distributed to tube 42 in third reagent-distributing position 70, and a reagent which can quickly react with the sample is distributed to tube 42 in fourth reagent-distributing position 72.

The reagents contained in vessels 50 held in second and third paths 46 and 48 can be distributed to reaction tubes 42 in any reagent-distributing position, that is, in position 58, position 60, position 70, or position 72. Hence, each reagent is distributed to tube 42 at one of these four positions 58, 60, 70 and 72, in accordance with the time it requires to react thoroughly with the sample.

Reaction tube 42 is further moved forward, and finally reaches colorimeter 104. Colorimeter 104 detects the color of the sample-reagent mixture contained in reaction tube 42.

After the color of the sample-reagent mixture has been detected, reaction tube 42 is moved to a washing/drying unit (not shown) and washed and dried by this unit, so that it can be again used for analyzing a sample.

In the analyzer described above, reaction tubes 42 are arranged in a circle, reagent vessels 50 are arranged in a smaller concentric circle, and other reagent vessels 50 are arranged in an even smaller concentric circle. Reagent vessels 56 are arranged in circles 52 and 54 along which reagent-distributing nozzles 82 and 84 can move. Vessels 50 contain reagents which are often used, and vessels 56 contain reagents which are seldom used or used in great quantities for analyzing the same item. Hence, when vessels 50 and vessels 56 are used in greater numbers, the number of vessels 50 containing reagents which are often used can be reduced.

Since fourth circle 52 intersects at two points with each of first, second and third circular paths 44, 46 and 48, and fifth circle 54 also intersects at two points with each of these circles 44, 46 and 48, nozzles 82 and 84 can each distribute two different reagents to the same reaction tube 42 in two positions. Therefore, it is possible to distribute various reagents to each reaction tube 42.

Figure 4:
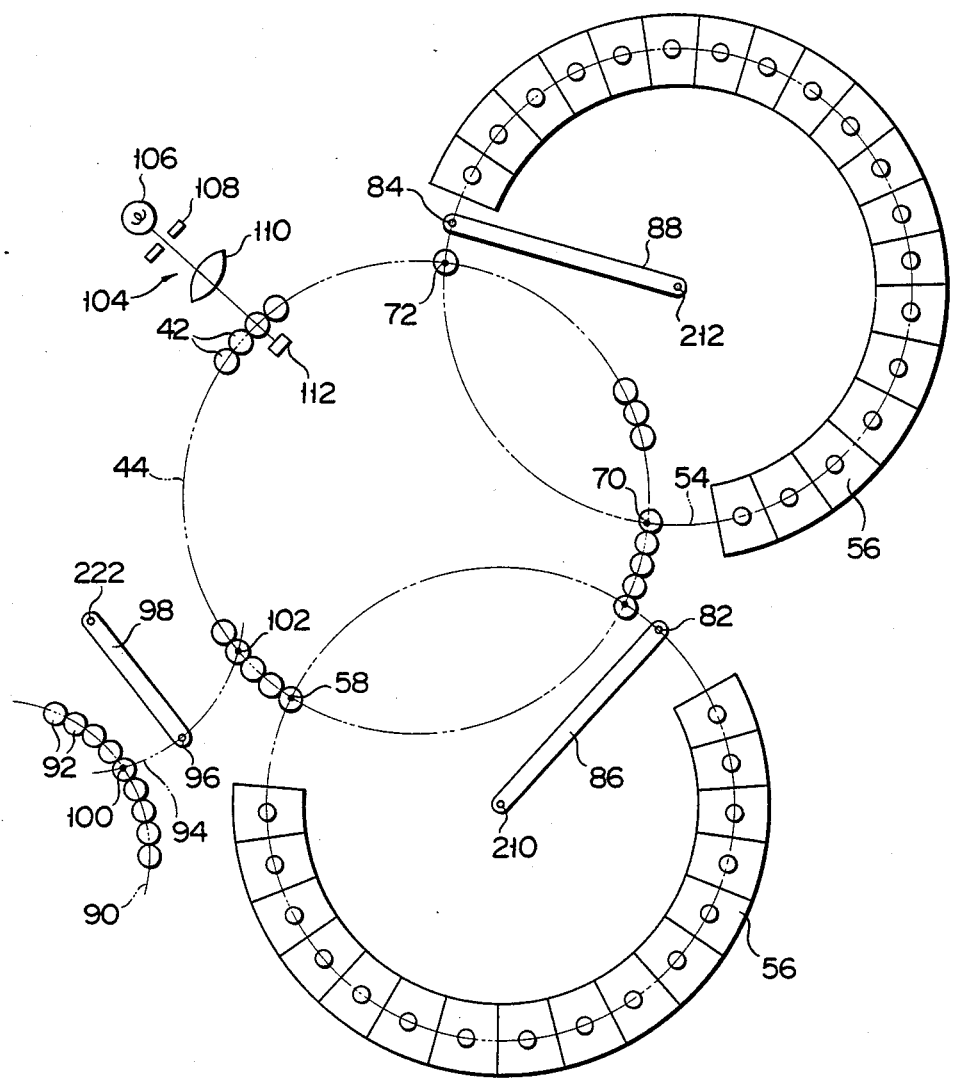
FIG. 4 is a diagram schematically illustrating part of an automatic chemical analyzer according to a second embodiment of the invention.

FIG. 4 schematically illustrates an automatic chemical analyzer according to a second embodiment of the present invention. This analyzer is identical to the first embodiment (FIG. 2), except that neither second turntable 164 nor third turntable 184 is provided. All reagents, that will be used, are contained in vessels 56 held in first and second arcuate paths 52 and 54. In the second embodiment, no reagent-vessels need to be moved. It suffices to rotate arms 86 and 88 in order to distribute any desired reagent to reaction tubes 42.

The present invention is not limited to the embodiments described above. Reagent vessels 56 can be set in arcs having an angle of less than 180°. Further, fourth and fifth circles 52 and 54 can be provided at different positions. Moreover, the number of arcs in which reagent-vessels 56 are held need not be limited to two. Still further, reagent-vessels 50 can be held in circular paths concentric with, surrounding, the circular path in which reaction tubes 42 are held. Furthermore, the number of circles, in which reagent-vessels 50 are held, need not be limited to two. In short, various changes and modifications can be made without departing the spirit and scope of the present invention.

What is claimed is:

1. An automatic chemical analyzer comprising:
   a plurality of reaction tubes;
   first holding means for holding said reaction tubes in a first circular path;
   first drive means for driving said first holding means to move said reaction tubes forward along the first circular path;
   sample-distributing means for distributing a sample to said reaction tubes;
   first reagent container means including plural first reagent vessels arranged concentric with said first holding means in a second circular path concentric with said first circular path, for containing a plurality of reagents in said first reagent vessels;
   second reagent container means including plural second reagent vessels for containing a plurality of second reagents, said second reagent vessels arranged in an arcuate portion of a third circular path which intersects the reagent tubes of said first circular path at a pair of reagent distribution points and which intersects the reagent vessels of the second circular path at a pair of reagent drawing points;
   second drive means for driving said first reagent container means such that selected of said first reagent vessels containing selected first reagents are located at said pair of reagent drawing points;
   reagent-distributing means having an nozzle movable in a circular path laterally coextensive with an orthogonal projection of said third circular path for drawing a selected second reagent from a selected second reagent vessel and dispensing said selected second reagent to a selected of said reaction tubes at a selected one of said pair of reagent distributing points and for drawing a selected first reagent from a selected of said first reagent vessels at a selected one of said pair of reagent drawing points and distributing the selected drawn first reagent to a selected reaction tube at a selected one of said pair of reagent distribution points; and
   control means for controlling said first and second drive means and said reagent-distributing means so that said nozzle draws a selected reagent from either one of said first reagent vessels at a selected one of said pair of reagent drawing points or one of said second reagent vessels and distributes the selected reagent to a selected reaction tube at a selected one of said pair of reagent distributing points.

2. The automatic chemical analyzer according to claim 1, wherein the second reagent vessels arranged at both ends of said arcuate portion are located near said first circulates path.

3. The automatic chemical analyzer according to claim 1, wherein said second reagent vessels are arranged outside said first circular path.

4. The automatic chemical analyzer according to claim 1, wherein said first reagent vessels are arranged inside said first circular path.

5. The automatic chemical analyzer according to claim 1, wherein said first holding means has a first annular turntable including said first circular path; and said second reagent container means has a second annular turntable including said second circular path, being concentric with said first annular turntable and surrounded by said first annular turntable.

* * * * *